United States Patent [19]

Kulik

[11] Patent Number: 4,936,857
[45] Date of Patent: Jun. 26, 1990

[54] PROSTHETIC PERICARDIUM

[76] Inventor: Yaroslav P. Kulik, 140, kv. 36, Blagoveschensk, ulitsa Zeiskaya, U.S.S.R.

[21] Appl. No.: 281,707
[22] PCT Filed: Feb. 15, 1988
[86] PCT No.: PCT/SU88/00036
§ 371 Date: Oct. 14, 1988
§ 102(e) Date: Oct. 14, 1988
[87] PCT Pub. No.: WO88/06027
PCT Pub. Date: Aug. 25, 1988

[30] Foreign Application Priority Data

Feb. 23, 1987 [SU] U.S.S.R. ............... 4197835

[51] Int. Cl.$^5$ ............................. A61F 2/22
[52] U.S. Cl. ............................. 623/3
[58] Field of Search ............. 623/3; 600/16, 17; 128/64

[56] References Cited

U.S. PATENT DOCUMENTS

| 3,371,662 | 1/1966 | Heid et al. ............. 128/64 |
| 3,513,836 | 9/1967 | Sausse ................... 128/64 |
| 4,497,074 | 2/1985 | Rey et al. ............. 623/1 |
| 4,536,893 | 8/1987 | Parravicini ........... 623/3 |
| 4,690,134 | 9/1987 | Snyders ................ 128/64 |

FOREIGN PATENT DOCUMENTS 8200649 1/1982 France .
1111752 7/1983 U.S.S.R. .

Primary Examiner—Randall L. Green
Assistant Examiner—Stephanie L. Iantorno
Attorney, Agent, or Firm—Ladas & Parry

[57] ABSTRACT

A prosthetic pericardium comprises a sheathing (1) made of a biologically neutral elastic material and sized to suit the heart's size, and provided with a means for its being fixed on the heart. The sheathing (1) is shaped as a figure-of-eight platelet one of whose loops (2) has a greater area than the other loop and is provided with a projection shaped as a reed (4) and located at its top. The fixation means is made as a guide channel (5) situated along the contour of the platelet accommodated in the channel (5) of a tube (6) made of an elastic material, and a flexible cord (7) accommodated in the tube (6) with a possibility of reciprocating therealong.

3 Claims, 4 Drawing Sheets

PROSTHETIC PERICARDIUM

TECHNICAL FIELD

The invention relates generally to medicine, more specifically to prosthetic organs of the human body and has particular reference to a prosthetic pericardium.

PRIOR ART

Known in the present state of the art is pery-guard the prosthetic pericardium which is in effect a rectangular flap made of the tissue of a bovine pericardium treated appropriately to eliminate the antigenic properties.

The known prosthetic pericardium is employed as patches for closure of a defect of the natural pericardium after surgery on the heart. However, such a patch fails to cover the entire heart and hence adhesions are liable to occur. Moreover, the heterotransplant of a bovine pericardium is rejected by the organism, and calcinosis is thus developed.

One more state-of-the-art prosthetic pericardium is known to comprise sheaths from a biologically neutral elastic material made to suit the heart's dimensins and provided with a means for its being fixed on the heart (SU, A, 1,009,457).

The sheath is shaped to suit the heart's shape and is open on the side of the base of the heart. A number of perforations are made in the sheath over the entire surface thereof. The fixation means of the known prosthetic pericardium is shaped as straps situated on the side of the open sheath end. Once the surgery on the heart has been completed the heart is placed in the hollow space formed by the sheath of the prosthetic pericardium, the aortic arch is encompassed by the straps passed through the transverse sinus, and the ends of the straps are stitched to the edge of the sheath. After the aforesaid manipulations have been completed the sheath of the prosthetic pericardium is reliably fixed on the heart so as to cover the entire surface thereof and establish an interposition between the outer cardiac surface and the inner surface of the natural pericardium, thus preventing formation of any adhesions therebetween. The perforations provide for the exchange with biological fluids between the cardiac surface and the pericardial cavity which may contain, e.g., a serous fluid that facilitates sliding of the cardiac walls during the cardiac contraction.

The prosthetic pericardium of such a construction should be selected to suit the heart's size, therefore a great number of standard sizes of the prosthetic pericardium are required to provide proper selection of an optimum variant. Fixation of the prosthetic pericardium on the heart by stitching it to the surface of the straps is inconvenient with the heart beating. Moreover, withdrawal of the prosthetic pericardium upon termination of the postoperative period involves thoracotomy, which renders the procedure more traumatic and leads to the outflow of the pericardial fluid.

DISCLOSURE OF THE INVENTION

It is an object of the invention to provide a prosthetic pericardium of such a construction that would ensure a possibility of withdrawing a prosthetic pericardium from the thoracic cavity without resorting to thoracotomy which renders the procedure less traumatic, prevents the pericardial fluid from flowing out of the natural pericardial cavity, and provides more versatility and convenience in operation.

The essence of the invention resides in a prosthetic pericardium, comprising a sheathing or membrane from a biologically neutral elastic material sized to suit the heart's size and provided with a means for its being fixed on the heart. According to the invention, the sheathing is shaped as a figure-of-eight platelet, one of whose loops has a larger area than the other and is provided with a reed-shaped projection situated at its top. A fixation means is shaped as a guide channel situated along the contour of the platelet so that a tube from an elastic material may reciprocate along said channel, and a flexible cord accommodated in the tube with the possibility of reciprocating with respect to the tube. The ends of the tube and the cord are brought out of the channel on the side of the reed-shaped projection.

To provide more convenient extraaction of the prosthetic pericardium the tube is to be composed of two equal-length portions, while the cord is composed of two portions, one of which is shorter and the other is longer than one of the tube portions by the same length.

It is desired to provide the platelet with holders for locking the electrode of a cardiostimulator in position.

The prosthetic pericardium, according to the present invention, can be extracted from the thoracic cavity without incision of the chest wall, through a wound sized up to 5 mm in the superior portion of the natural pericardium and a skin incision 5 to 6 mm long. No injury to the heart or its surrounding tissues occurs, including the natural pericardial tissues, so that no outflow of the pericardial fluid occurs from the natural pericardial cavity.

The prosthetic pericardium, according to the invention, does not require careful selection of its size, is more versatile and convenient in operation, and requires no fixing stitches to attach it on the heart.

SUMMARY OF THE DRAWINGS

In what follows, the invention will become more apparent from a description of a specific embodiment thereof with reference to the accompanying drawings, wherein.

PREFERRED EMBODIMENT OF THE INVENTION

Figure 1:
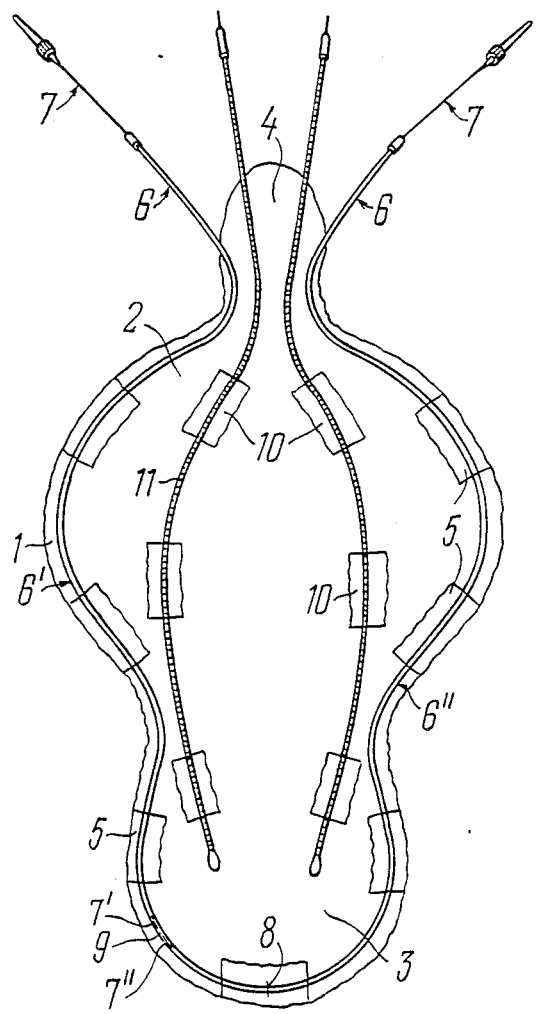
FIG. 1 is a schematic plan view of prosthetic pericardium, according to the invention.

The prosthetic pericardium as illustrated in FIG. 1 comprises a sheathing 1 made from a biologically neutral elastic material, e.g., polyurethane, and a means for fixing the sheathing 1 on the heart. The sheathing 1 is shaped as a figure-of-eight platelet one of whose loops 2 has a greater area than its other loop 3. A projection shaped as a reed 4 is provided at the top of the loop 2. The fixing means incorporates a guide channel 5 situated along the contour of the platelet, a tube 6 from an elastic material, e.g., polyurethane placed in the channel 5 so as to reciprocate along the axis of the channel 5, and a flexible cord 7 accommodated in the tube 6 with a possibility to reciprocate with respect to the tube. The channel 5 is composed of a number of separate sections distributed lengthwise the platelet contour; however, the channel may also be made nonsectional throughout the length of the platelet contour. As a rule the channel 5 is made of the same material as the sheathing 1. In this particular embodiment of the prosthetic pericardium the tube 6 is constituted by two equal-length portions 6' and 6" adjacent to each other at a point 8 at the top of the smaller loop 3. The flexible cord 7 is also constituted by portions 7' and 7" but unequal in length, i.e., the portion 7' is shorter and the portion 7" is longer than one of the portions 6' and 6" of the tube 6 by the same length. As a result the ends of the portions 7' and 7" of the cord 7 adjoin each other at a point 9 inside the portion 6' of the tube 6 in order to hold the two sections of tube 6', 6" together. The other ends of the tube 6 and of the cord 7 are brought out of the channel 5 on the side of the reed 4 so as to project beyond the sheathing 1. In addition, holders 10 carrying electrodes 11 of a cardiostimulator are secured on the surface of the sheathing 1. The holders 10 are shaped as short channels whose cross-sectional dimension is comparable with the diameter of the endoelectrode 11, said channels being made from a polyurethane film and secured on the surface of the sheathing 1.

Figures 3, 4:
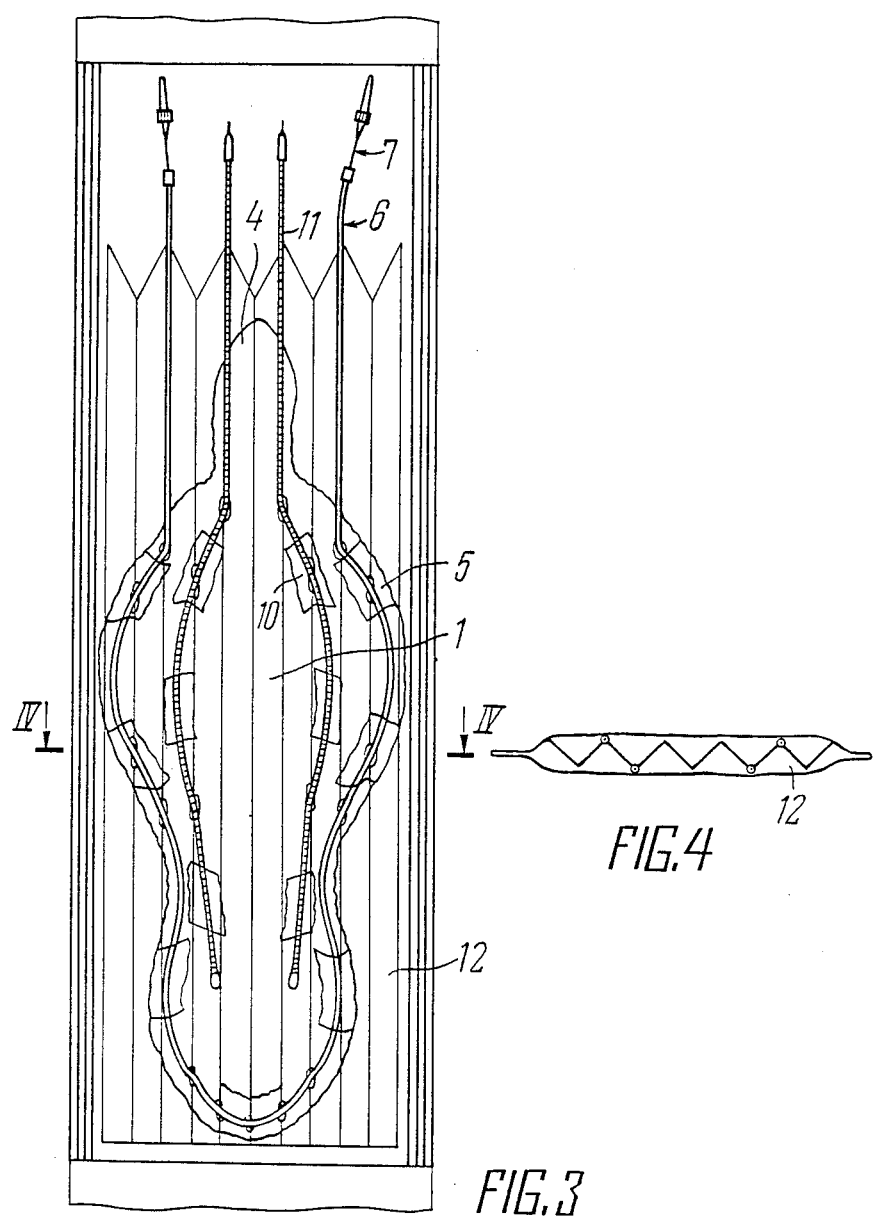
FIG. 3 is the prosthetic pericardium of FIG. 1 when enclosed in a sterile package.
FIG. 4 is a section taken along a line IV—IV in FIG. 3.

The prosthetic pericardium, according to the invention, should be kept in a hermetically sealed sterile package 12 (FIGS. 3, 4) till its use in surgery.

The prosthetic pericardium, according to the invention, is applied as follows.

Figure 2:
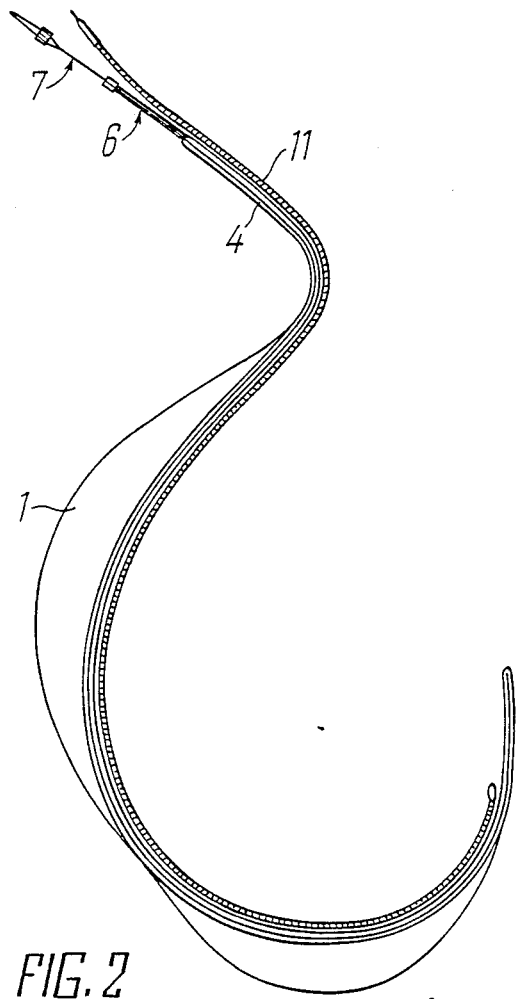
FIG. 2 is a side view of FIG. 1 showing the prosthetic pericardium in a position when fixed on the heart.
Figure 5:
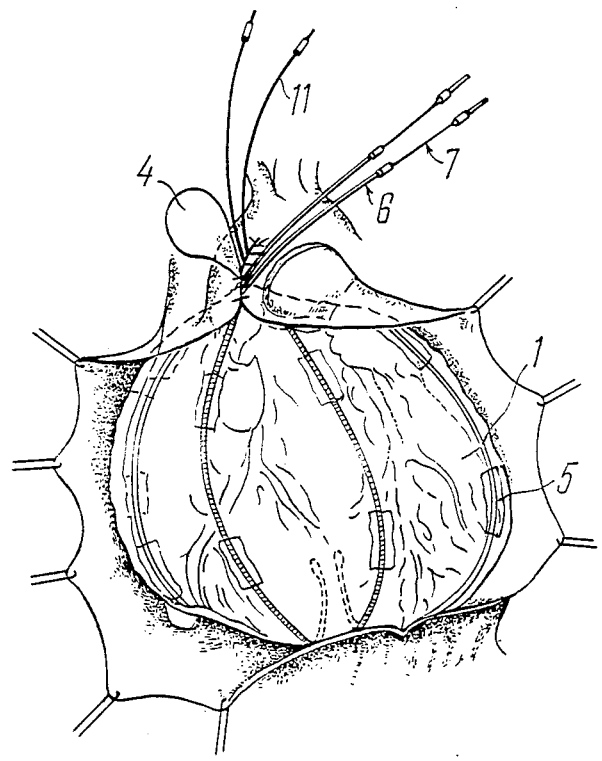
FIG. 5 is an isometric view of a heart and a prosthetic pericardium when inserted in the natural pericardial cavity.

Upon completing a correcting surgical procedure on the heart before hermetically suturing the natural pericardium, the prosthetic pericardium is withdrawn from the sterile package 12 (FIG. 3) and is placed under the posterior cardiac surface as far as the base of the heart, with the smaller loop 3 (FIGS. 1, 2), while the larger loop 2 covers the entire cardiac surface and partly the vessels at the front. As a result, the prosthetic pericardium assumes the position shown in FIG. 2. The natural pericardium is then sutured tightly leaving a wound up to 5 mm long through which the reed 4 (FIG. 5) of the prosthetic pericardium is brought outside along with the ends of the tube 6 and of the cord 7, which are placed under the skin. Then the skin is stitched up. 10 to 12 days later a skin incision 5 to 6 mm long is made above the reed 4 of the prosthetic pericardium and the ends of the tube 6 and of the flexible cord 7 are brought through the incision along with the reed 4. Then there are successively withdrawn the portions 7' and 7" of the cord 7, next the portions 6' and 6" of the tube 6, and the sheathing 1 of the pericardium by taking hold of the reed 4.

Application of the herein-disclosed prosthetic pericardium makes it possible to dispense with thoracotomy for its withdrawal, its construction does not require careful selection of its size. Withdrawal of the prosthetic pericardium inflicts no injury upon the heart and its surrounding tissues. Installation of the prosthetic pericardium, according to the invention, involves no additional manipulations for its holding on the heart, and its withdrawal causes no outflowing of the pericardial fluid from the natural pericardial cavity.

Industrial Applicability

The invention is aimed at application in surgery on the heart to prevent adhesion formation processes that might occur within the postoperative period between the heart and the natural pericardium.

I claim:

1. A prosthetic pericardium dimensioned to fit about the heart comprising a sheathing (1) formed from a biocompatible elastic material and provided with fixation means for fixing said sheathing on the heart said sheathing being shaped in the form of a figure-of-eight platelet having a perimeter and two loop portions, one of the loop portions (2) of said platelet having a larger area than the other of said loop portions, said one loop portion being provided with a projection shaped as a reed, said reed situated on said one loop portion at a position opposite said other loop portion, said fixation means comprising a guide channel (5) situated along the perimeter of said platelet, a tube (6) formed from an elastic material reciprocatingly mounted within said channel, and a flexible cord (7) reciprocatingly mounted within said tube, the ends of said tube (6) and said cord (7) exiting from said channel at a position on said one loop portion opposite said other loop portion.

2. A prosthetic pericardium as claimed in claim 1 wherein the tube (6) comprises two equal-length portions (6', 6"), while the cord (7) comprises two portions (7', 7"), one of which is shorter and the other of which is longer than each of said equal length portions (6') of the tube (6) by the same length.

3. A prosthetic pericardium as claimed in claim 1 wherein said platelet is provided with holdes (10) for fixing electrodes (11) of a cardiostimulator.

* * * * *